United States Patent
Nakaie et al.

(10) Patent No.: US 6,582,968 B2
(45) Date of Patent: Jun. 24, 2003

(54) PARAMAGNETIC AND ACTIVE ANALOGUE (EMP-2) OF MELANOCYTE STIMULATING HORMONE CONTAINING AMINO ACID-TYPE STABLE FREE RADICAL

(75) Inventors: Clóvis Ryuichi Nakaie, São Paulo (BR); Eduardo Maffud Cilli, São Paulo (BR); Maria Tereza Lamy-Freund, São Paulo (BR); Simone dos Reis Barbosa, São Paulo (BR)

(73) Assignee: Conselho Nacional de Desenvolvimento Cientifico e Technologico PROJUR/CNPq/AC, Brasilia (BR)

( * ) Notice: Subject to any disclaimer, the term of this patent is extended or adjusted under 35 U.S.C. 154(b) by 0 days.

(21) Appl. No.: 09/935,760

(22) Filed: Aug. 24, 2001

(65) Prior Publication Data

US 2002/0137682 A1 Sep. 26, 2002

Related U.S. Application Data

(63) Continuation of application No. PCT/BR00/00025, filed on Feb. 23, 2000, now abandoned.

(30) Foreign Application Priority Data

Feb. 24, 1999 (BR) ............................................. 9900595

(51) Int. Cl.$^7$ .................. A61K 38/00; G01N 24/00; C07K 4/00
(52) U.S. Cl. ................. 436/174; 530/412; 530/300; 436/173
(58) Field of Search ..................... 514/2, 14; 436/176, 436/173, 182, 174; 530/402, 412, 300

(56) References Cited

PUBLICATIONS

Barbosa, S. R. et al. (1999) "First synthesis of a fully active spin–labeled peptide hormone" FEBS Letters, vol. 446, pp. 45–48.*
K. Hofmann, et al., "Studies on Polypeptides. XX. Synthesis and Corticotropic Activity of a Peptide Amide Corresponding to the N–Terminal Tridecapeptide Sequence of the Corticotropins," *Journal of the American Chemical Society*, vol. 83, pp. 2289–2291, May 20, 1961.
A. Rassat et al., "No. 145—Nitroxydes. XXIII–Préparation d'aminoacides radicalaires et de leurs sels complexes," Bull. Soc. Chim. Fr. 815, pp. 815–817, 1967.
E. Gross, et al., Eds., "The Peptides: Analysis, Synthesis and Biology—vol. 2 Special Methods in Peptide Synthesis, Part A," *Academic Press*, 1980.
C.R. Nakaie, et al., "pH Dependence of EPR Spectra of Nitroxides Containing Ionizable Groups," *Brazilian J. Med. Biol. Res.*, vol. 14, pp. 173–180, 1981.
E. London, et al., "Fluorescence Quenching in Model Membranes. 1. Characterization of Quenching Caused by Spin–Labeled Phospholipid." *Journal of the American Chemical Society*, vol. 26, No. 7, pp. 1932–1938, 1981.

C.R. Nakaie, et al., "Synthesis and Properties of Spin–Labeled Angiotensin Derivatives," *Biochimica et. Biophysica Acta*, vol. 742, pp. 63–71, 1983.
M. Castrucci, et al., "Melanotropin Bioassays: In Vitro and in Vivo Comparisons," *General and Comparative Endocrinology*, vol. 55, pp. 104–111.
D.N. Chaturvedi, et al., "Synthesis and Biological Evaluation of the Superagonist [$N^\alpha$–Chlorotriazinylaminofluorescein–Ser$^1$,Nle$^4$, D–Phe$^7$]–α–MSH," *Journal of Pharmaceutical Sciences*, vol. 74, No. 3, pp. 237–240, Mar. 1985.
L.J. Berliner, et al., "Spin–Labeling—Theory and Applications," *Biological Magnetic Resonance*, vol. 8, Plenum Press, 1989.
M. Castrucci, et al., "Melanotropic Peptide Antagonists: Recent Discoveries and Biomedical Implications," *Drugs of the Future*, vol. 15. No., pp. 41–54, 1990.
K.G. Mountjoy, et al., "The Cloning of a Family of Genes That Encode the Melanocortin Receptors," *Science*, vol. 257, pp. 1248–1251, Aug. 28, 1992.
H. Vaudry, et al., Eds., "The Melanotropic Peptides," *Annals of the New York Academy of Sciences*, vol. 680, May 31, 1993.
S. M. Miick, et al., "Short alanine–based peptides may form $3_{10}$–helices and not α–helices in aqueous solution," *Letters to Nature*, vol. 359, No. 15, pp. 653–655, Oct. 1992.
S.D. Sharma, et al., "Melanotropic peptide–conjugated beads for microscopic visualization and characterization of melanoma melanotropin receptors," *Proc. Natl. Acad. Sci.*, USA 93, pp. 13715–13720, 1996.
E.M. Cilli, et al., "Correlation between Solvation of Peptide–Resins and Solvent Properties," *J. Org. Chem.*, vol. 61, No. 25, pp. 8992–9000, 1996.
W. Fan et al., "Role of melanocortinergic neurons in feeding and the agouti obesity syndrome," *Nature*, vol. 385, No. 9, pp. 165–168, Jan. 1997.
R. Marchetto, et al., "A Novel Spin–Labeled Amino Acid Derivative for Use in Peptide Synthesis: (9–Fluroenylmethyloxycarbonyl)–2,2,6,6–tetramethylpiperidine–N–oxyl–4–amino–4carboxylic Acid," *Journal of the American Chemical Society*, vol. 115, No. 23, pp. 11042–11043, 1993.
H. Wessels, et al., "Synthetic Melanotropic Peptide Initiates Erections in Men with Psychogenic Erectile Dysfunction: Double–Blind, Placebo Controlled Crossover Study," *The Journal of Urology*, vol. 160, 389–393, Aug. 1998.

* cited by examiner

*Primary Examiner*—Karen Cochrane Carlson
*Assistant Examiner*—Samuel Wei Liu
(74) *Attorney, Agent, or Firm*—Morrison & Foerster LLP

(57) ABSTRACT

The present invention relates to an α-melanocyte stimulating hormone (α-MSH) analogue, labeled with an amino acid-type paramagnetic spin probe, for example, Toac, or 2,2,6,6-tetramethylpiperidine-1-oxyl-4-amino-4-carboxylic acid, and methods for the synthesis thereof. The preferred analogue of the invention, acetyl-Toac$^0$-α-MSH (abbreviated as EPM-2) is the first such analogue that maintains entirely the natural α-MSH activity.

10 Claims, 5 Drawing Sheets

FIG. 2A
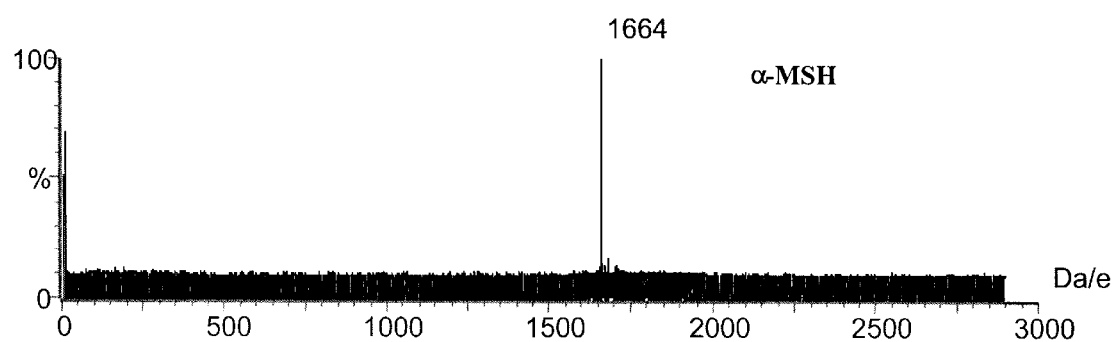
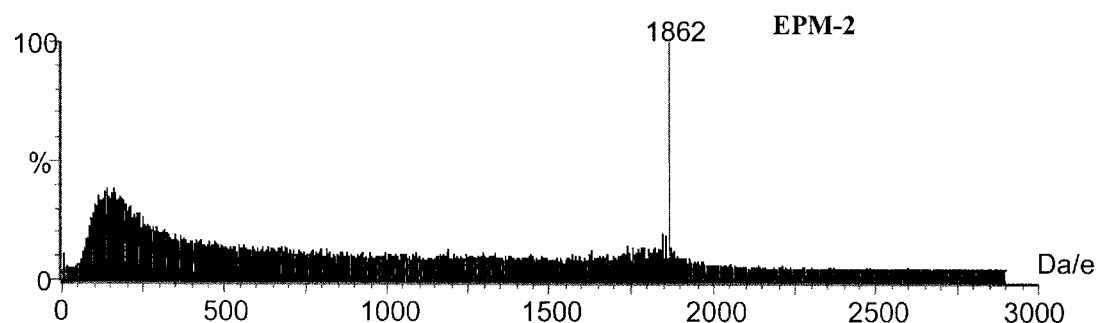
FIG. 2B

FIG. 3A
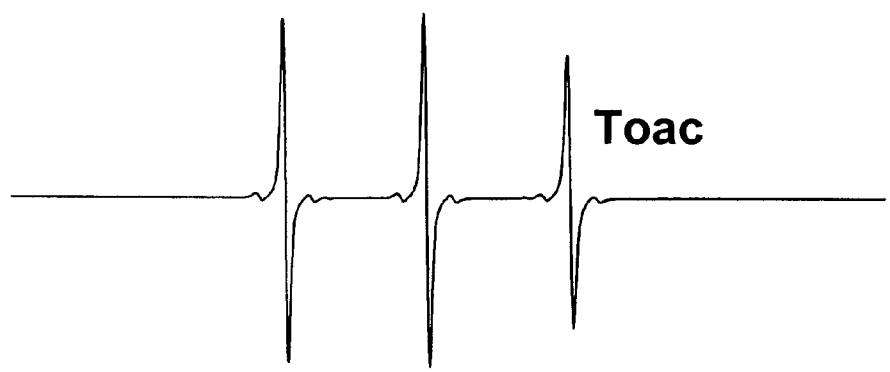
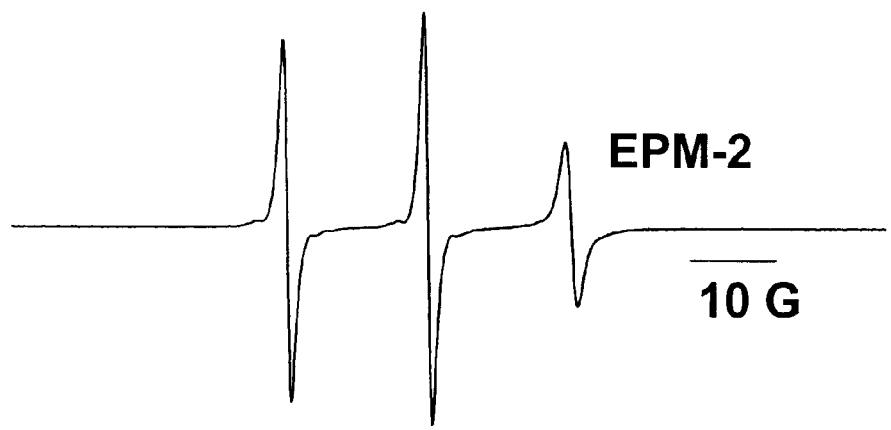
FIG. 3B

PARAMAGNETIC AND ACTIVE ANALOGUE (EMP-2) OF MELANOCYTE STIMULATING HORMONE CONTAINING AMINO ACID-TYPE STABLE FREE RADICAL

REFERENCE TO RELATED APPLICATION

This application is a continuation of International Application No. PCT/BR00/00025, filed Feb. 23, 2000, now abandoned, the contents of which are incorporated by reference herein.

BACKGROUND OF THE INVENTION

1. Field of the Invention

The invention relates to the chemical synthesis of a melanocyte stimulating hormone (α-MSH) analogue containing a stable amino acid-type free radical (spin probe or spin label) that maintains entirely the biological activity of the native hormone. This maintenance of α-MSH biological potency and the presence of the paramagnetic spin label in its structure allow this analogue to be studied through electron paramagnetic resonance (also known as EPR or RPE, depending on the language used, English or Portuguese) and contains relevant potentialities for several additional applications in the biochemical-medical fields, related to the investigation of several already known physiological effects of this hormone.

2. Technical Background and Prior Art

The melanocyte stimulating hormone (α-MSH) seems to be involved in several physiologic processes in higher animals (e.g. The Melanotropic Peptides, Vaudry, H & Eberle, N, eds., New York, 1993). Among these processes one may mention the effect upon the fetal growth, behavior, inflammation (e.g. Drugs of the Future, 15, 41[1990]), obesity [Nature 385, 165 (1997)], erectile function, [J. Urol. 160, 389 (1998)], etc. No matter what, the more relevant effect of this hormone considered as a neuroimunemodulator, is related with the skin darkening effect (The Melanotropic Peptides, New York, [1993]).

The skin darkening of mammals and of other animals is basically controlled by the amount of melanin, a biological compound synthesized from the amino acid tyrosine and mediated by the enzyme tyrosinase. The melanin molecules are stored inside granules of cellular structures denominated melanocytes, and it has been observed that the more aggregated these granules in the cells are, the clearer the individual's skin will become. The control of this granular aggregation in the organism is carried out by a compound known as melatonin (N-acetyl-5-methoxy-tryptamine). Contrariwise, darker skin is due to more dispersed melanin-containing granules in the cells, and this dispersion control in the organism is performed by the aforementioned α-MSH, which is a peptide found in the pituitary gland of several animal species, including the human, and its amino acid sequence is already known, as represented below:

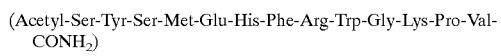

(Acetyl-Ser-Tyr-Ser-Met-Glu-His-Phe-Arg-Trp-Gly-Lys-Pro-Val-CONH$_2$)

Therefore, besides the importance of this hormone to the physiological effects already mentioned, a better understanding of the α-MSH effect can be useful, for example, for possible elucidation of the causes or mechanisms of several diseases regarding irregular pigmentation of the skin. And in some lower animals, this peptide hormone is also very important because it allows alterations of the color of the skin as a function of the ambient luminosity, thus facilitating the survival of some species.

The first chemical synthesis of this peptide was made some decades ago (J. Am. Chem. Soc. 83, 2289 [1961]) and recent researches on this important hormone have aimed at clarifying its action mechanism at the cellular membrane level, because its specific receptor was already characterized and found in different tissues and organs (Science 257, 1248 [1992]), including tumor cells (Proc. Natl. Acad. Sci. USA 93, 13715 [1996]). For this, several approaches are applied, among which many are spectroscopic, so that, besides furnishing conformational information of the hormone in solution, they can also supply details on interaction and positioning in synthetic or natural membranes.

Within this context, a more potent α-MSH analogue has for instance already been labeled with fluorescent probes in specific positions of its sequence for further conformational and structural studies and for detection of its cellular receptor (J. Pharm. Sci. 74, 237 [1985]).

Prior to this application, there has not been published an α-MSH analogue containing a paramagnetic compound (spin probe or spin label) that maintains entirely its original biological activity. The usefulness of hormone labeling with this special type of marker molecule has the advantage of, for the first time, facilitating the application of the RPE method already mentioned [Spin Labeling—Theory and Applications, Berliner, L.J., New York, 1989] for the investigation of this important tridecapeptide hormone.

In contrast with other spectroscopic methods, ESR permits the detection of conformational alterations of the hormone either in solution or associated with macrostructures such as membranes, based on spectral data that monitor the degree of motion of the molecule or of the system where the spin probe is bound. In addition, owing to the fluorescent quenching property of the nitroxide function of the spin label (Biochemistry, 20, 1932 [1981]) the ESR method allows a unique alternative approach for conjugation as compared with the conventional fluorescence method.

However, the most important pre-requisite in any strategy of introducing a spin marker in the α-MSH molecule or in any other biological molecule of interest is the need for maintenance of original biological potency. It is not so probable that it is as different from the radioactive labeling of hormone which does not modify its chemical structure, a non-natural compound and with significant size is being inserted in the structure of the native hormone under study. Besides this pre-requisite, it was also necessary that the introduction of the spin probe in the hormone structure should be in such a way as to reflect closely the peptide conformational features. For this reason, spin labels that bind to the hormone through a great amount of chemical bonds (long spin probes) and therefore, with high rotation freedom were not considered to be very appropriate. This is the case in some examples referred to in the literature where a long and flexible marker was used for ESR study of peptides, e.g. Nature 359, 653 (1992). The ideal case would be, therefore, a paramagnetic probe that binds as rigidly as possible to the peptide structure and directly in its skeleton through a peptide bond as usually happens with amino acid residues.

The inventors initiated the use, some decades ago, of an amino acid-type spin probe abbreviated as Toac (2,2,6,6-tetramethylpiperidine-1-oxyl-4-amino-4-carboxylic acid)—e.g. Bull. Soc. Chim. Fr. 815 (1967) in the peptide chemistry field, and it seemed to fulfill partially these requirements for binding more rigidly to the structure of the hormone. By containing the amine and carboxylic groups in a same carbon of the heterocyclic Toac structure, this spin label can be introduced as an amino acid directly to the peptide backbone.

To make it possible to couple in a peptide sequence through the classic solid phase peptide synthesis methodology, [e.g. Peptides: Analysis, Synthesis and Biology (Barany, G. and Merrifield, R. B. 1980)], the tert-butyloxycarbonyl group was introduced (Boc) in the Toac amino group function, according to Braz. J. Med. Biol. Res. 14, 173 (1981). Due to the lability of the free radical nitroxide group in a strong acid medium present during the peptide synthesis method (trifluoroacetic acid), its introduction was only possible in the N-terminal position of the peptide structure e.g. Biochim. Biophys. Acta, 742, 63 (1983). Later on, this limitation of the use of ESR in peptides was also overcome by the inventors, when using another Toac-amino group protection, the base labile 9-fluorenylmethyloxycarbonyl (Fmoc), in J. Am. Chem. Soc. 115, 11042 (1993). With this protecting group we demonstrated for the first time in the literature a way of introducing the spin probe Toac at any internal positions of the peptide hormone structure, making possible therefore the substitution of any residue of amino acid of its original sequence for this paramagnetic compound. A great variety of examples of application of this strategy were later published, but none of them had reported the synthesis of a spin labeled biologically active peptide that maintained entirely its natural potency.

SUMMARY OF THE INVENTION

The invention here described includes the synthesis by chemical methods of an α-melanocyte stimulating hormone analogue labeled with Toac which maintains 100% of its natural biological activity.

The chemical structure of the α-MSH synthesized in accordance with this invention is the following:

(Acetyl-Toac-Ser-Tyr-Ser-Met-Glu-His-Phe-Arg-Trp-Gly-Lys-Pro-Val-CONH$_2$) (SEQ ID NO:1)

This structure will be referred in this application as Ac-Toac$^0$-α-MSH or EPM-2.

BRIEF DESCRIPTION OF THE DRAWINGS

FIGS. 2A and 2B are a depiction of the mass spectra of the α-MSH and EPM-2 peptides, respectively.

FIGS. 3A and 3B are depictions of the EPR spectra of $10^{-4}$ M Toac and EPM-2, respectively, in aqueous solution.

DETAILED DESCRIPTION OF THE INVENTION

Figure 1:
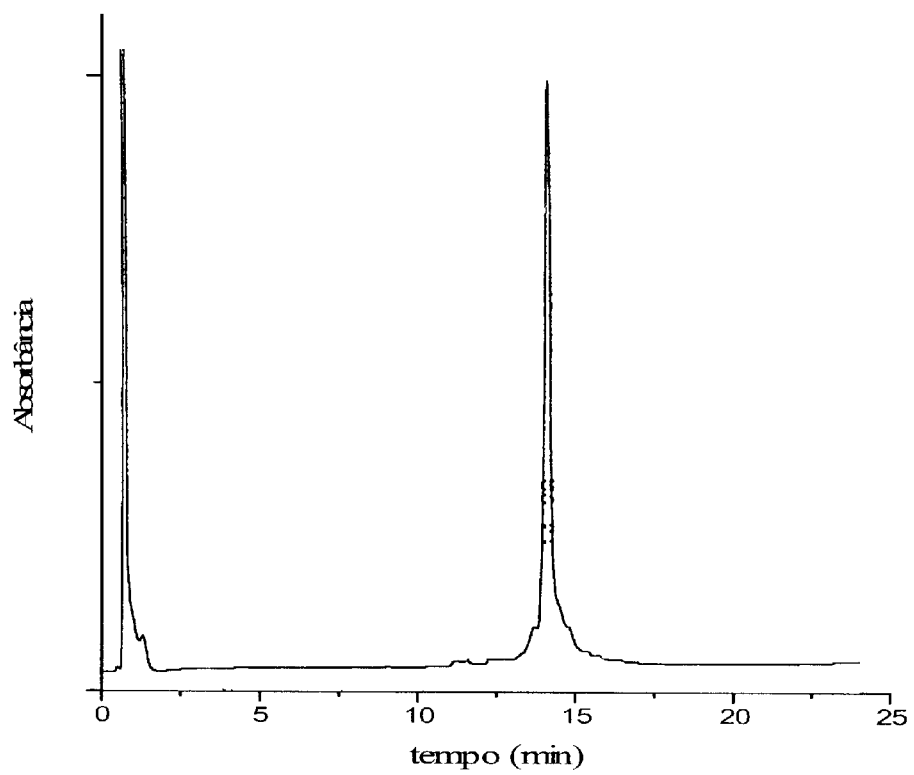
FIG. 1 is a graph of an HPLC (high performance liquid chromatography) profile of the purified EPM-2 peptide.

We have discovered that the strategy of coupling the spin probe Toac in the N-terminal portion is due to the fact that previous studies have shown that this position is less essential for the maintenance of the α-MSH activity. As we have found the presence of the acetyl group in the amino terminal group of the sequence is also necessary for this activity, we carry out this acetylation step after the Toac incorporation. The general solid phase chemical methodology for peptide synthesis was applied for this sequence where the temporary protecting group Boc is used for peptide chain elongation bound to the starting polymer. The resin used was methylbenzidrylamino-resin, a toluoylmethylamine-containing a copolymer of styrene and 1% divinylbenzene for linking of the C-terminal residue of the sequence, vide, Peptides 2, 45 (1981). The reactive side chains were protected temporarily with appropriate chemical groups.

In each synthetic cycle, the Boc protecting group is removed with 30% TFA (v/v) in dichloromethane (DCM) treatment for 30 min and the following deprotonation of the amine group of the sequence for coupling step is carried out in diisopropylethylamine, 10% v/v, in DCM for 10 minutes.

The coupling reaction of amino acids is usually done with the acylating agent diisopropylcarbodiimide in DCM/DMF (1:1) for about 2 hours. The monitoring of this important synthesis reaction is carried out with the ninhydrin test, and if recoupling is needed, the acylating agent is changed to tetrafluoroborate-2-(1H-benzotriazolyl-1,1,3,3-tetramethyluronium), i.e., TBTU. The choice of the solvent system for each synthesis cycle followed the method introduced recently by the inventors, based on a new solvent polarity parameter that considers the sum of the acceptor (AN) and donor (DN) electron properties of the solvents, see, J. Org. Chem. 61, 8992 (1996). The selected solvent for the α-MSH synthesis based on this study was N-methylpyrrolidinone (NMP).

The introduction of the Toac probe was performed using its Fmoc derivative and followed the already mentioned synthesis strategy which allows the introduction of this spin label internally to the peptide sequence. The acetylation step was done using a large excess of acetic anhydride in DMF for 1 h and in general, we did not observe relevant difficulties in the assembly of this acetylated tetradecapeptide.

The cleavage of peptide from the resin was carried out in anhydrous HF for 90 min at 0° C. In this reaction, ethanedithiol was added for the Trp formyl-group removal and cresol and dimethylsulfide to minimize side reactions during this acid treatment. The proportion of these components was: HF:o-cresol:dimethylsulfide:ethanedithiol (8.5:0.5:0.5:0.5). After the cleavage the resin is rinsed with ethyl acetate for removal of by-products and the desired peptide was extracted from the resin with 5% acetic acid and lyophilized. A white powder material was obtained with a final yield of 83%.

Comparative Alkaline Treatment for the Reversion of Nitroxide Protonation After HF Cleavage The insertion of the Toac molecule in a peptide sequence needs an additional alkaline treatment for reversion of the nitroxide protonation that occurs during HF cleavage. As there is no systematic study showing the most effective and quickest method of this reversion known up to now, we decided to test comparatively different basic conditions for this reversion. We observed that the more efficient reversion protocol was aqueous ammonium hydroxide solution at pH 10 for 2 hours at 50° C. The monitoring of the reversion rate was based on the analytical HPLC retention time of both Toac protonated and unprotonated forms. Due to its higher polarity the protonated form eluted faster than the parent component.

Purification of the Peptide

The crude peptide subjected to the alkaline reversion was purified in preparative HPLC with a C18 column (25 for 300 mm) in an acetonitrile/water gradient containing 1% of TFA. The main fraction isolated in this chromatogram yielded after lyophilyzation, 37 mg of a white powder, whose purity is represented in the analytical HPLC shown in FIG. 1. The results shown in FIG. 1 were derived using an ODS (octadecyl silane) (4.6×150 mm) column and elution with linear gradient 5% to 95% B in 30 min, a flow rate of 1.5 mL/min and detection at 220 nm. Solvent A was 0.1% TFA in H$_2$O; and solvent B was 0.1% TFA in 60% acetonitrile/H$_2$O.

The purity of this material was also proven by mass spectroscopy with a MALDI-type apparatus (matrix assisted desorption ionization) from Micromass. FIG. 2 shows the expected 1862 molecular weight peak of the EPM-2 against the 1664 molecular weight peak of native α-MSH. The correct composition of this sample was also checked by amino acid analysis in a Beckman model 6300 analyzer. The following relative proportions of amino acids were found: (the theoretical values are in parentheses): 1.95 Ser (2), 1.03 Met (1); 1.01 Glu (1); 0.96 His (1); 0.98 Phe (1); 0.97 Arg (1); 1.04 Trp (1); 0.97 Gly (1); 1.05 Lys (1); 0.95 For (1) and 1.01 Val (1). The acid hydrolysis carried out includes dissolution of the peptide in HCl (6 N) degassed (with $N_2$) solution containing 0.5% phenol and left for 72 h at 110° C. in a Pyrex capped vial. As the Trp residue is decomposed by this acid treatment, the peptide was hydrolyzed by the p-toluenosulfonic acid method. The peptide was subjected to this treatment for 72 h and further diluted with a pH 2.2 buffer before being injected in the amino acid analyzer column.

Besides all these analytic characterizations applied for the spin labeled peptide, RPE spectroscopy was also used to confirm the paramagnetic signal of the sample. FIG. 3 displays the ESR spectrum of the labeled hormone after purification and diluted in ammonium acetate solution (0.05 M, pH 5.0), as compared to the free Toac in the same conditions.

Biological Activity Assay

The biological activity assay of the EPM-2 was carried out comparatively to the native α-MSH. The classical method of measuring by reflectance the alteration in the frog skin pigmentation was assayed, see, Gen. Comp. Endocrinol. 55, 104 (1984). The potency of the synthesized hormone was determined through a dose-effect curve and long lasting activities were measured until a maximum of 3 h after the peptide removal from the incubation system carried out with successive washes.

Briefly, the skin of the thigh and the dorsal portion of a frog were removed and cut in pieces of 2×2 cm which were placed among two rings of PVC and maintained for 1 h in Ringer's solution. After this period, the melanin granules aggregate in the melanocytes, and the skin becomes clearer. When α-MSH or its spin labeled analogue is added to the medium, there is a dispersion of the pigments in the cell, resulting in skin darkening. The change in the coloration is therefore monitored (decrease in the skin reflectance) in a photovolt reflectometer. The result is expressed as percentage in relation to the initial value.

Figure 4:
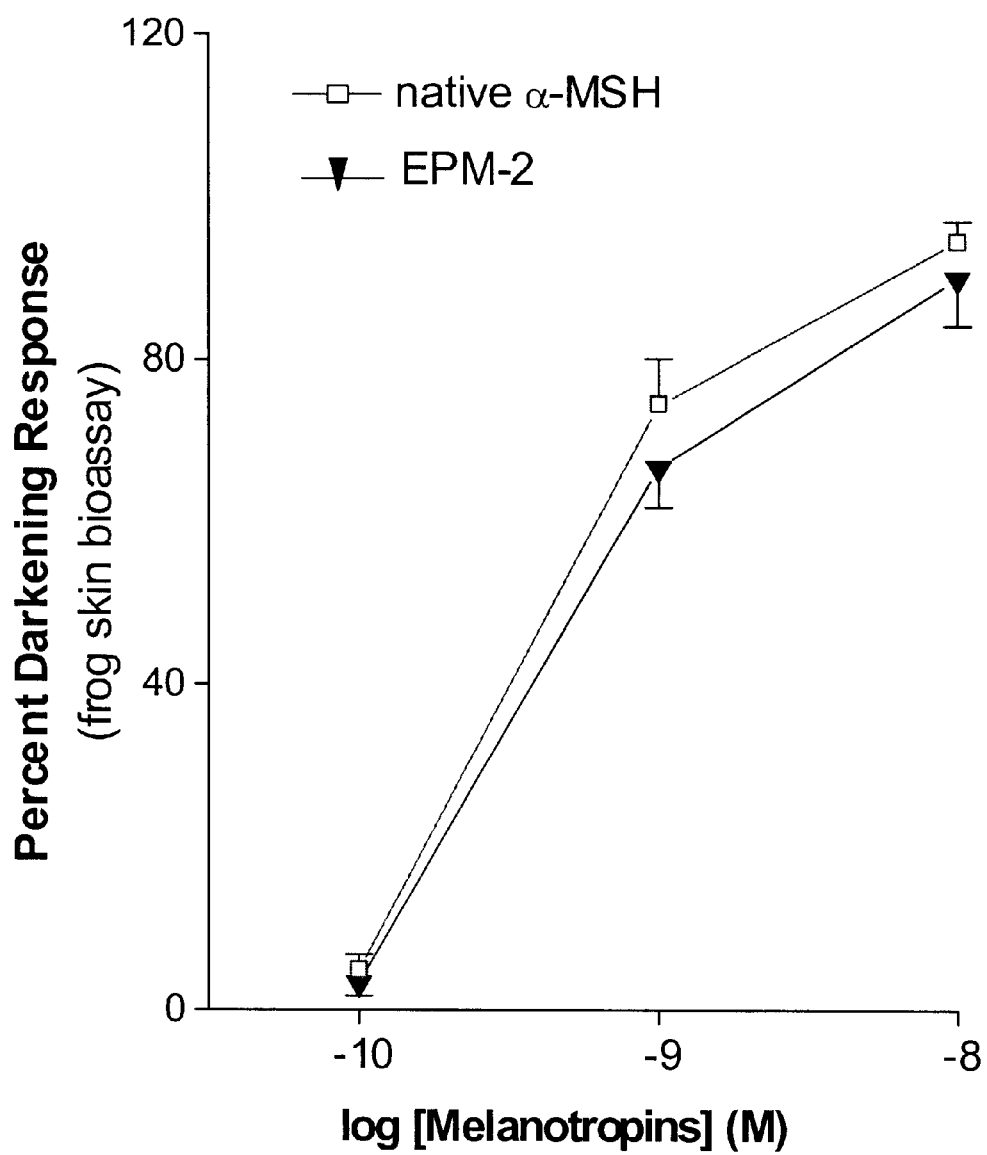
FIG. 4 is a graph of dose-response curves to EPM-2 as compared to native α-MSH, in a frog (*Rana catesbeiana*) skin bioassay.

The labeled analogue is clearly a full α-MSH agonist with equivalent potency as can be seen in FIG. 4.

Figure 5:
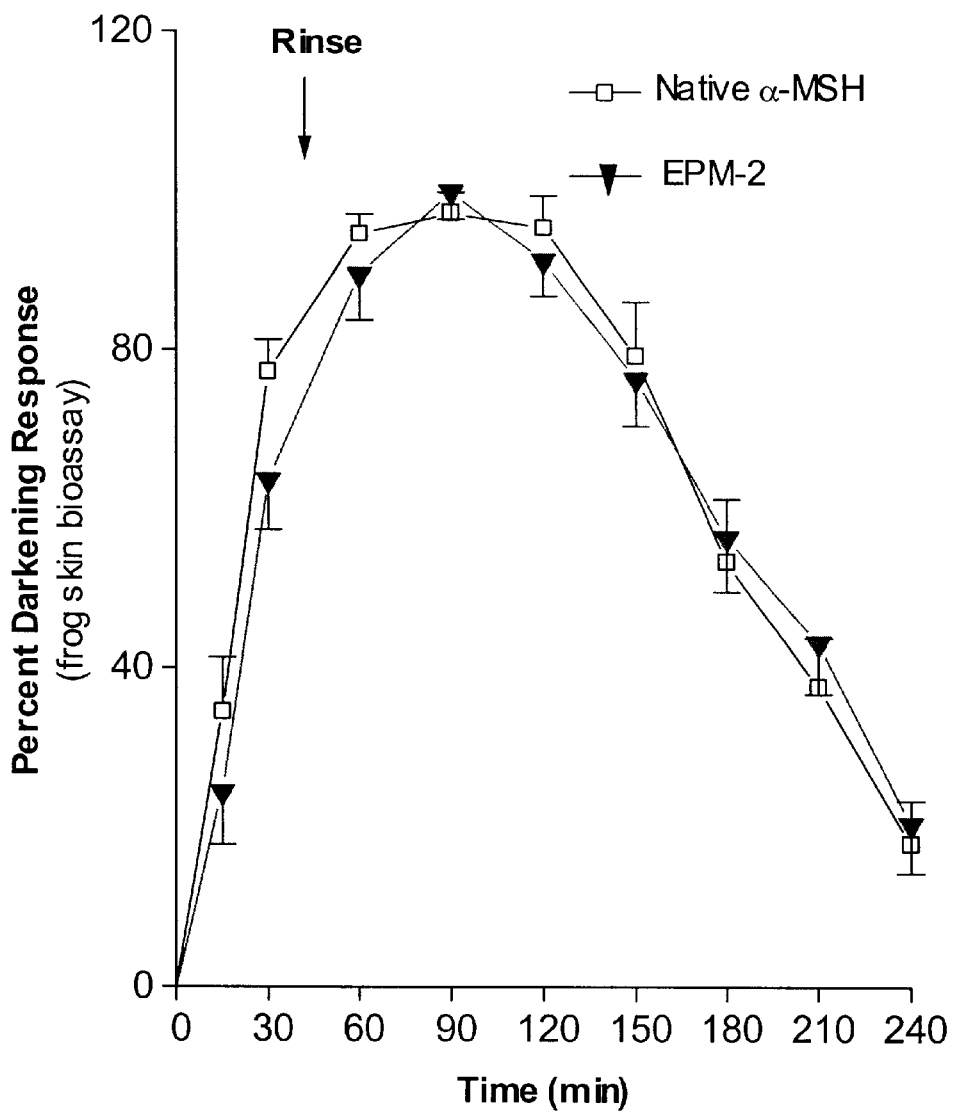
FIG. 5 is a graph showing the reversal of the maximal responses to the native hormone and to EPM-2 ($10^{-8}$ M) after removal of the peptides and rinsing of the preparation.

In addition, after the removal of the agonist and followed by several Ringer's solution washings, the reversal of the maximum response for the labeled analogue was obtained after 90 min, with the same speed of the native hormone (FIG. 5).

By containing the spin probe Toac in its structure and for fully maintaining the biological potency of the native α-MSH, the novel chemical product herein described and denoted EPM-2 may be of practical application in the following situations:

As a Comparative Model Compound for Investigation of Active α-MSH Conformation

The knowledge of the correct α-MSH action mechanism in vertebrates can be better investigated by using the EPM-2 derivative. This is due to the fact that by containing a paramagnetic group in its structure, its conformational features may be evaluated with the ESR spectroscopic method. Initially, variations of pH, temperature, ionic strength and the amount of organic solvents in the medium can be performed in solution and analyzed with reference to the ESR spectra of this paramagnetic peptide hormone.

The influence of the organic solvents trifluoroethanol (TFE) and hexafluoroisopropanol (HFPI), known to induce secondary structures such as the α-helix, might be also investigated. Complementarily to the ESR method, this conformational approach can be also carried out with other spectroscopies such as circular dichroism, nuclear magnetic resonance and fluorescence. In these last two methods, for possessing the property of suppressing resonance or absorption/emission effects respectively, the paramagnetic peptide of this invention may be employed in a great variety of comparative spectroscopic studies.

The above detailed conformational studies can be extended to internal regions of macrostructures such as lipid bilayers and artificial membranes. This approach mimics the native hormone conformation when inserted in a common biological membrane. By taking into account an other property of the ESR method, the molecular association of paramagnetic compounds can be studied based on the spin-spin interaction phenomenon that occurs between spin probes but strongly dependent on the average distance among these molecules, e.g. Spin Labeling—Theory and Applications, (Berliner, L.J., New York, 1989). Thus, in addition to the sensitivity to detect the molecular interactions inside these macrostructures, it is also possible to further estimate intermolecular distances, regardless of the system.

EPM-2 is also useful as a molecular probe for detection, quantification and characterization studies of the α-MSH receptor. The utility of Toac will be dependent on the fluorescence quenching effect induced by the nitroxide function. The use of radioactive or fluorescent agonists has been the most common strategy to localize, quantify and characterize membrane receptors. One may therefore detect and quantify receptor-containing cells and how they are positioned throughout cell membranes. The more appropriate methods so far used for localization, quantification and characterization of membrane receptors use fluorescent agonists, as this strategy is less dangerous and the agonist which will bind to the receptor presents higher chemical stability than the parent radioactive analogue.

Thus, by taking into account the fluorescence quenching property, Toac-labeled α-MSH will, in brief, be useful for:

α-MSH Receptor Visualization, Localization and Characterization

As fluorescent α-MSH analogue has been already synthesized for receptor binding studies, the use of the EPM-2 fluorescent quenching property may be of value, for instance, for checking receptor localization and quantification. As there are modern methods to visualize receptors in cell cultures, frozen cell slices and cell fragments in vitro or in vivo, one may predict a relevant EPM-2 utility for help elucidate the action mechanism of this hormone when bound to the receptor.

Quantification of Cell Lines Containing α-MSH Receptors

This important information at the receptor level may be obtained by modern biochemical methods such as flow cytometry, in which one can identify and characterize common cells lineages as containing or not containing the α-MSH receptor.

Investigation of Receptor-Fluorescent Hormone Binding

The mechanism and the kinetics of interaction investigation of the fluorescent α-MSH derivative with its receptors can be improved with the use of EPM-2. This peptide will be also valuable for monitoring bindings of other analogues or chemical products that possess the common property in binding to α-MSH receptor.

As a Proteolytic Enzyme Substrate or Inhibitor

In the case where an evaluation the peptide hormone towards enzyme degradation is desired, the presence of Toac radical will be of value as it will supply details of molecular mobility related to enzymatic peptide degradation, either in solution or internally to several types of macrostructures (natural membranes, lipid bilayers, polymer beads, cells, etc).

As a Chemical Product with Therapeutic Potentiality

Due to the participation of α-MSH in different physiological processes, this fully active paramagnetic analogue may be useful as a drug, alone or conjugated with others having therapeutic properties. The fact that its both extremities are blocked and also contains internally a non-natural Toac probe may impart to this peptide higher stability against degradation inside the organism, thus increasing its potential as a drug for some specific cases.

What is claimed is:

1. Acetyl-(2,2,6,6-tetramethylpiperidine-1-oxyl-4-amino-4-carboxylic acid)-Ser-Tyr-Ser-Met-Glu-His-Phe-Arg-Trp-Gly-Lys-Pro-Val-CONH$_2$ (SEQ ID NO:1).

2. A method of synthesizing a paramagnetic and biologically active analogue of α-melanocyte stimulating hormone, comprising
introducing a paramagnetic group internally into α-melanocyte stimulating hormone peptide sequence by means of an acylating agent.

3. The method of claim 2, wherein the paramagnetic group is derived from 2,2,6,6-tetramethylpiperidine-1-oxyl-4-amino-4-carboxylic acid.

4. The method of claim 2, further comprising introducing an amino-terminal acetyl-group by a solid phase method into the sequence after the introducing of the paramagnetic group, where tert-butyloxycarbonyl (boc) is used as a temporary α-amine group protector for peptide chain elongation and methyl-benzhydrylamine-resin and a styrene-1% divinylbenzene copolymer containing toluyl-methylamine groups are used for coupling of the C-terminal residue of the sequence.

5. The method of claim 4, comprising boc group cleavage carried out by treatment in trifluoroacetic acid 30% (v/v) in dichloromethane for 30 minutes followed by the deprotonation of the amine group, carried out in basic diisopropylethylamine, 10% v/v in dichloromethane solution for 10 min.

6. The method of claim 4, comprising using diisopropylcarbodiimide in dichloromethane/dimethylformamide (1:1) as an acylating agent for about 2 hours, and monitoring the acylation with a colorimetric ninhydrin test.

7. The method of claim 6, further comprising recoupling an additional amino-terminal group into the sequence with 2-(1H-benzotriazolyl-1,1,3,3-tetramethyluronium) tetrafluoroborate.

8. The method of claim 3 or 4, comprising using 9-fluorenylmethyloxycarbonyl as a protection agent to allow introduction of the spin probe at internal positions the peptide sequences and carrying out a final acetylation step using acetic anhydride in dimethylformamide for about 1 hour.

9. The method of claim 4, further comprising cleaving the synthesized peptide from the resin with anhydrous HF for about 90 min at 0° C., extracting the peptide from the resin with 5% acetic acid in water and lyophilizing the extracted peptide.

10. The method of claim 4, further comprising an alkaline treatment of crude peptide for nitroxide deprotonation and purification of the treated crude peptide with the use of an acetonitrile/water gradient.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ser Met Glu His Phe Arg Trp Gly Lys Pro Val
 1               5                  10